United States Patent [19]
Weissman et al.

[11] Patent Number: 6,121,249
[45] Date of Patent: Sep. 19, 2000

[54] TREATMENT AND PREVENTION OF CARDIOVASCULAR DISEASES WITH HELP OF ASPIRIN, ANTIOXIDANTS, NIACIN, AND CERTAIN B VITAMINS

[75] Inventors: Donald L. Weissman, P.O. Box 15927, Beverly Hills, Calif. 90209; Jerry Rosenbaum, Miami, Fla.

[73] Assignee: Donald L. Weissman, Beverly Hills, Calif.

[21] Appl. No.: 09/108,765

[22] Filed: Jul. 1, 1998

[51] Int. Cl.[7] ............................ A61K 31/70; A61K 31/60
[52] U.S. Cl. ............................................. 514/52; 514/165
[58] Field of Search ........................................ 514/52, 165

[56] References Cited

U.S. PATENT DOCUMENTS

| | | |
|---|---|---|
| 4,008,719 | 2/1977 | Theeuwes et al. . |
| 4,452,783 | 6/1984 | Marks et al. . |
| 4,687,808 | 8/1987 | Jarrett et al. . |
| 5,041,430 | 8/1991 | Addicks et al. ........................ 514/161 |
| 5,053,429 | 10/1991 | Hirsch et al. . |
| 5,084,482 | 1/1992 | Hirsch et al. . |
| 5,326,569 | 7/1994 | Acosta et al. . |
| 5,385,937 | 1/1995 | Stamler et al. . |
| 5,401,730 | 3/1995 | Sauvage et al. ........................ 514/165 |
| 5,427,799 | 6/1995 | Valentine et al. . |
| 5,446,131 | 8/1995 | Maraganore . |
| 5,466,469 | 11/1995 | Kuhrts . |
| 5,612,382 | 3/1997 | Fike . |
| 5,626,884 | 5/1997 | Lockett . |
| 5,656,620 | 8/1997 | Ismail . |
| 5,703,073 | 12/1997 | Garvey et al. . |
| 5,770,215 | 6/1998 | Moshyedi ................................ 424/440 |

OTHER PUBLICATIONS

Zuger, Abigail, "The Other Drug Problem: Forgetting to take them," *The New York Times*, Jun. 2, 1998, §F, p. 1, c. 2, The New York Times Co.

*Primary Examiner*—Raymond Henley, III
*Attorney, Agent, or Firm*—Pillsbury Madison & Sutro LLP

[57] ABSTRACT

Disclosed is the method of reducing the incidence and severity of atherosclerosis, atherosclerotic central nervous system disease, claudication, coronary artery disease, homocystine related disorders, hypertension, peripheral vascular disease, presenile dementia and/or restenosis in humans by daily administration of an effective amount of a combination of acetylsalicylic acid (ASA), at least one antioxidant, a cyanocobalamin compound (Vitamin B12), a folic acid compound, a pyridoxine compound (Vitamin B6) and a niacin compound.

20 Claims, 2 Drawing Sheets

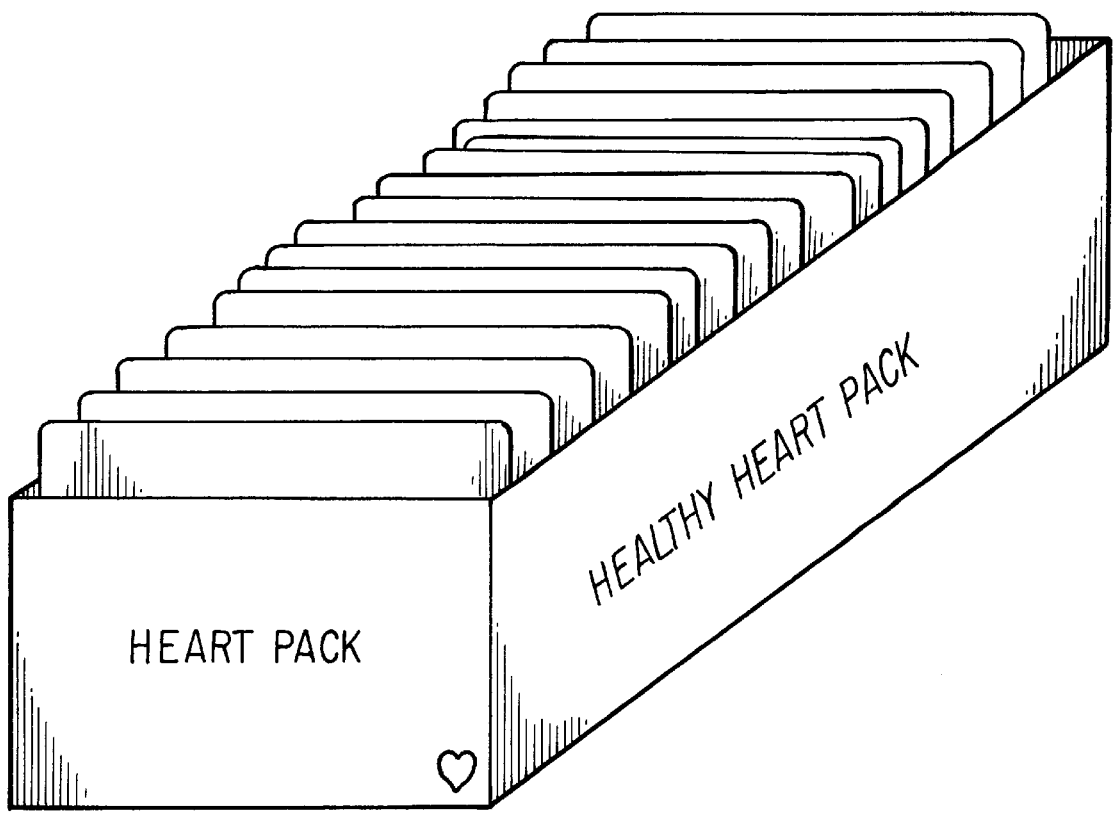
One month supply of 30 packs
1 package per day
"Exhibit 1"

← 3" →

| HEALTHY HEART | |
|---|---|
| Ingredients | |
| ASPIRIN | 81 mg. |
| FOLIC ACID | 900 mg. |
| $B_6$ | 50 mg. |
| $B_{12}$ | 100 mg. |
| VITAMIN E | 400 i.u. |
| VITAMIN C | 500 mg. |
| NIACIN | 100 mg. |

3"

Exhibit 2

TREATMENT AND PREVENTION OF CARDIOVASCULAR DISEASES WITH HELP OF ASPIRIN, ANTIOXIDANTS, NIACIN, AND CERTAIN B VITAMINS

BACKGROUND OF THE INVENTION

1. Field of the Invention

This invention relates to a combination of aspirin, antioxidant, niacin, and vitamins to prevent cardiovascular diseases, to a daily administration pack for such combination to facilitate the patient's compliance with prescription to take such combination, and to the method of treating and preventing cardiovascular diseases with the help of such combination.

Cardiovascular disease ranks as the leading cause of mortality and morbidity in the United States today. This year, it is estimated that 1.5 million people will have a heart attack and that one third of those will die as a result of CAD.

The American College of Cardiology recently identified other abnormalities as factors for which intervention is likely to lower heart disease risk. Elevated total blood cholesterol is frequently considered a risk factor for coronary artery disease (CAD), but it is important to note that in the Framingham study 80% of CAD patients had the same total cholesterol as those who did not develop CAD.

2. Definition of Certain Terms

Throughout the specification and associated claims, terms listed below shall be read as having the meaning here stated.

| | |
|---|---|
| CAD | Coronary artery disease |
| LDL | Low density lipoprotein |
| IDL | Intermediate density lipoprotein |
| MI | Myocardial infarction |
| PVD | Peripheral vascular disease |

3. Prior Art

Heredity remains the number one risk factor in heart disease; 77% of people in the United States with heart disease have inherited metabolic traits contributing to their atherosclerosis. Lp (a) is a LDL with protein (a) attached, and elevated level of Lp (a) is an inherited trait present in approximately 33% of heart disease patients. Elevated levels of Lp(a) increase the risk of heart disease by 300%, yet Lp (a) is not detected in traditional lipid profile tests. A powerful predictor of heart attacks in young men and of vein graft blockage following bypass surgery, elevated levels of Lp(a) also increase the danger of other risk factors. High Lp(a) can be treated with niacin.

Niacin (nicotinic acid) or niacinamide is a member of the Vitamin B-complex group (vitamin B3). Buoyant LDL's are the lighter, larger LDLs found primarily in LDL pattern A people. Dense LDL's are the heavier, smaller LDLs found primarily in LDL pattern B people. LDL density change is the strongest predictor of percent change in coronary artery stenosis. There is substantial evidence that reduction in small LDL is more important than reduction in LDL-cholesterol in achieving improvements. Following treatment with niacin, small LDL subclass patterns significantly improve with a larger LDL diameter. This is also associated with improvement in other abnormalities such as elevated IDL, elevated LP (a) and enhanced postprandial lipemia.

The chief drawback of using niacin in the treatment of hyperlipidemia is facial and truncal flushing, which occurs in nearly all users shortly after ingestion of a tablet with as small a dosage as 75 mg of niacin.

It appears that niacin induces flushing by increasing the formation and/or release of some prostaglandin, which in turn increases the production of cyclic amp. Aspirin is a prostaglandin inhibitor and reduces the incidence and severity of flushing.

Aspirin therapy has been well established as a platelet aggregate inhibitor and is now widely used. It has been shown to be the strongest therapeutic known to reduce the risk of a first heart attack in healthy individuals.

Recent evidence suggests that elevated blood levels of homocystine, which is derived from the amino acid methionine, is linked to heart disease. Homocystine is a sulfur-containing amino acid formed during the metabolism of methionine.

Homocystine increases the formation of highly atherogenic oxycolesterols, increases lipid peroxidation, and increases the oxidation of LDL in vitro. These observations suggest a potential role for antioxidant therapy in ameliorating homocystine-dependent oxidative vascular injury. Patients with mild hyperhomocystinemia have none of the clinical signs of severe hyperhomocystinemia and are typically asymptomatic until the third or fourth decade of life when premature CAD develops, as well as recurrent arterial and venous thrombosis. How the body metabolizes, or breaks down, homocystine can be determined genetically. People who inherit a defective gene for homocystine metabolism tend to have elevated homocystine blood levels—a trait found in 20–30% of patients with atherosclerosis.

Three B-vitamins, folate and vitamins B6 and B12 play essential roles as cofactors in homocystine metabolism. Elevated plasma homocystine (even because of genetic variants) can usually be normalized by moderate vitamin supplementation. Folic acid alone, folic acid combined with B12 and B6, and vitamins B6 and B12 have all been shown to reduce homocystine concentrations. Normalization of the plasma homocystine concentration usually occurs within four to six weeks after the initiation of therapy, but may occur in as little as two weeks. Interestingly, the reduction in mortality from cardiovascular causes since 1960 has been correlated with the increase in vitamin B6 supplementation in the food supply.

A retrospective analysis of dietary vitamin C and E intake was done in the CLAS trial (n=156) and indicated an association between supplementary vitamin E intake and angiographically demonstrated reduction in coronary artery lesion progression.

The Cambridge Heart Attack and Antioxidant Study studied 2002 CAD patients, randomized to 800 IU vitamin E per day or placebo for 1.5 years, and revealed a significant reduction in non-fatal MI in the vitamin E group.

In recent years, however, awareness has grown that any medication regimen is only as good as as the patient's compliance with it, that is that prescribed medications are actually taken at the times and in the amounts prescribed. The problem, and some ingenious but labor intensive and costly attempts to solve it, is well summarized in an article "The Other Drug Problem: Forgetting to Take Them" by science writer Abigail Zuber (New York Times, June 2, 1998), which is here incorporated by reference in its entirety and from which the following is excerpted.

> Study after study over the last 20 years has shown that misuse of prescription drugs is a worldwide epidemic every bit as dangerous and costly as an actual medical illness. It was tagged "America's other drug problem" in the early 1990's when researchers consistently found it responsible for 10 to 25 percent of hospital and nursing home admissions studied. In 1984, the National Pharmaceutical Council, an association of pharmaceutical companies, estimated that misuse of prescription drugs had caused 125,000 deaths a year from heart disease alone. In 1993 the same organization calculated that not taking medicines correctly was draining upwards of $100 billion a year from the nation's economy in direct and indirect costs.

And with increased cost consciousness has come a new appreciation of the problem of "noncompliance," as medicine has labeled the phenomenon of skipping some doses, doubling up on others, forgetting to refill at the end of the month or taking a few of a family member's antibiotics on the chance they will work better than the ones prescribed.

Interest has been sharpened by new studies clearly demonstrating that disorders like elevated blood cholesterol or asthma respond far better when patients take medications as prescribed. And the flip side of the equation has been vividly illustrated by the medications for tuberculosis and AIDS: they may actually damage a patient's health when taken improperly, by inducing drug-resistant disease that may be passed on to others and cannot be treated at all.

In fact, improving medication-taking behavior may be one of the few arenas in health care today where widely disparate interest groups—including medical researchers, patient advocates, drug companies, public health authorities and H.M.O. executives—share a goal. The result: an outpouring of medical articles and studies on the subject and a cornucopia of new tactics, devices and programs all aiming to cajole patients to remember their pills . . . .

"People in general take about 75 percent of their medications as prescribed," said Joyce Cramer, a medical researcher at Yale University and an authority on drug-taking behavior. But within that figure the range of misbehavior is wide. Nancy Houston Miller, a nurse who is the associate director of Stanford University's Cardiac Rehabilitation Program in Palo Alto, estimated that 10 to 20 percent of patients grossly flout medication regimens—never filling the prescriptions or taking only a few token pills. About 50 percent take doses more or less correctly. And an all-important 30 to 40 percent in the middle are "partial compliers," forgetful enough that the medication may have only a fraction of its desired effect or may actually be harming them, but well-intentioned and able to be trained to do better . . . .

Patients with serious diseases who are veterans at taking medication—cardiac-transplant patients, for instance—are usually better pill takers than those with silent conditions like high blood pressure, Dr. Urquhart said. But in general, predicting what patient will display which pill-taking behavior often yields surprises.

Income, education, sophistication and competence in other parts of life correlate only very poorly with pill-taking behavior, the experts agree. People who know the purpose of the medication and the way it is supposed to work often do better than others. But education has its definite limits in inducing good pill-taking behavior—doctors, for example, are notoriously poor at it. In one large study of heart-attack prevention in male doctors in the 1980's, a full 30 percent of doctors were disqualified because they proved unable to take a single pill reliably every day.

Thus, as valuable as educational brochures, package inserts and videotapes may be, they are often now supplemented with a range of new compliance tools.

Some tools are million-dollar, labor-intensive programs. At Stanford, for instance, Ms. Miller has shown that heart-attack patients assigned to a nurse who spends hours educating them about diet, smoking, exercise and drug treatment, and then makes follow-up phone calls at home, are far more likely to stay on their medications than those who receive standard medical care.

Similarly, in New York City, a program in which city health department workers actually hand tuberculosis patients their medications every morning and watch them swallow has been credited with substantially increasing cure rates for the disease in the last five years.

Other new gadgets encourage patients to supervise themselves. A famous prototype for these devices was the circular container developed in the 1960's to help women remember their daily oral contraceptive pill. Flat blister-packs of prescription medications are now widely used in Europe to serve the same purpose, Dr. Urquhart said.

At the AIDS clinic at Yale-New Haven Hospital, every patient is supplied with a large rectangular pillbox whose 28 compartments can hold a week's worth of medications to be taken several times a day, said Dr. Gerald Friedland, a professor of medicine at Yale who directs the AIDS program. Current treatment for AIDS requires patients to take up to two dozen pills daily, often with different requirements for each, like an empty or a full stomach. "What's special about H.I.V. infection is the sheer complexity of the medications," Dr. Friedland said. "One of the definite predictors of poor adherence to treatment is the complexity of the regimen."

Other gadgets now on the market include simple electronic alarms that can be programmed to sound at intervals throughout the day, like the ALR tag made by TDI, and more sophisticated beepers that flash messages ("Time to take a gemfibrozil now," one made by Medprompt might tell patients with heart disease) as well.

And the newest devices entering offices and clinics can actually provide patients with little monthly medication report-cards, for both patient and doctor to inspect and try to improve.

They are pill-bottle caps fitted with a battery and a computer chip that remembers every time the bottle cap is opened and closed. Once a month the chip's memory can be downloaded into a computer and turned into a graph of exactly when during the month the patient dipped into the vial.

New York Times, Science Times, Jun. 2, 1998, Hirsch et al. U.S. Pat. No. 5,084,482 discloses a novel method employing compositions containing as an active antioxidant or anti-inflammatory agent the amino acid methionine, and/or one or more related compounds. This disclosure is based on the discovery that certain methionine or methionine-type companies in the dl-form or d-form at relatively high well-tolerated doses are potent antioxidant and anti-inflammatory agents in man and animals. The methionine compounds in high daily dosage thus may act in vivo to inhibit oxidative effects. All the preferred methods include at least one methionine compound.

Stamler U.S. Pat. No. 5,385,937 discloses administration of a nitrosating compound, such as nitroglycerin, nitric oxide etc and related compounds for the treatment or prevention of disease states resulting from hyperhomocystinemia.

Valentine et al. U.S. Pat. No. 5,427,799 disclose sustained release composition and method utilizing xanthan gum and an active ingredient such as niacin or analgesic. Xanthan gum and an excipient promotes sustained release.

Kuhrts U.S. Pat. No. 5,466,469 discloses a Granular Drug Delivery System utilizing a gel-forming dietary fiber and pharmaceutically active compound.

Fike U.S. Pat. No. 5,612,382 discloses a composition for percutaneous absorption of pharmaceutically active ingredients aspirin, vitamins, vasodilators, and/or analgesics in hydroxyalkyl amide as carrier for transdermal treatment of certain ailments Lockett U.S. Pat. No. 5,626,884 discloses a maintenance regime with controlled intake of particular vitamins, mineral and micronutrient formulations, drastically reducing the incidence and severity of sickle cell disease crisis.

Ismail U.S. Pat. No. 5,656,620 discloses treatment and prophylaxis of pain involving administration of vitamin E combined with salicylic acid in a pharmaceutically acceptable carrier or adjuvant.

Against this background there remains a need for improved formulations, and improved presentation thereof for facilitated compliance with prescribed medication including such formulations, for preventing coronary heart disease and peripheral vascular disease.

SUMMARY OF THE INVENTION

Definitions given below are used in the following disclosure of the invention and the claims.

ASA. Aspirin, i.e. all forms of acetylsalicylic acid including buffered aspirin, enteric coated aspirin, aspirin salts such as calcium acetylsalicylate, and mixtures of aspirin with acid acceptors. ASA does not include salicylic acid and its salts.

Niacin. Nicotinic acid or pyridine-3-carboxylic acid as the free acid, its salts and its amide also known as niacinamide.

Vitamin B6. Pyridoxine hydrochloride in all physiologically acceptable forms.

Vitamin B12. Cyanocobalamin in all physiologically acceptable forms.

Vitamin C antioxidant. Ascorbic acid in all physiologically acceptable forms including any one or more of the free acid, buffered ascorbic acid, calcium ascorbate, magnesium ascorbate, fat soluble esters such as ascorbyl palmitate, and associated bioflavanoids such as citrus bioflavanoids, hesperidin, quercetin, and rutin.

Vitamin E antioxidant. Alpha-tocopherol in all physiologically acceptable forms including natural d-alpha- tocopherol with mixed tocopherols including beta-, delta-, and gamma-tocopherol and Vitamin E dl alpha tocopheryl acetate.

Folic acid. Folate in all physiologically acceptable forms usually free folic acid.

In accordance with this invention, the incidence and severity of CAD and PVD in humans is reduced by daily administration of an effective amount of a combination of ASA acetylsalicylic acid, at least one antioxidant, a cyanocobalamin compound (Vitamin B12), a folic acid compound, a pyridoxine compound (Vitamin B6) and niacin. As a result of unexpectedly favorable interaction of these ingredients in certain proportions, the amounts of each required for effectiveness are modest, thus enabling avoidance of side effects and facilitating compliance with a prescribed regimen.

Also in accordance with this invention, compliance with a prescription to take the combination of this invention is facilitated by the provision of a single package combination including the quantities of ASA acetylsalicylic acid, at least one antioxidant, a cyanocobalamin compound (Vitamin B12), a folic acid compound, a pyridoxine compound (Vitamin B6) and niacin to be administered once daily. A number of such single package combinations can be assembled in an over-pack to provide treatment for a month or longer as prescribed by the practitioner.

Within the single package combination, the quantities of acetylsalicylic acid (ASA), at least one antioxidant, a cyanocobalamin compound (Vitamin B12), a folic acid compound, a pyridoxine compound (Vitamin B6) and niacin can be presented in a single dosage form or in a plurality of dosage forms as found convenient. Thus, to prevent flushing sometimes caused by niacin administration to a sensitive person, ASA can be included in the single package combination as a separate unit dosage form and taken 30 to 60 minutes in advance of niacin-containing dosage form or forms.

Further in accordance with this invention, atherogenic risk is diminished in 80% of the population and as a result the need for expensive blood analysis and monitoring is substantially reduced and in many cases eliminated.

In a human subject, daily administration of the combination of the invention over a period of several days provides a decrease in serum levels of homocystine, decreased coagulability decreased serum levels of intermediate density lipoprotein (IDL) and dense low density lipoprotein (LDL), and decreased oxidative damage. Thus lifelong therapy is prudent.

Daily administration of the combination of the invention can provide a number of therapeutic benefits to the recipient in improving all conditions that benefit from reduction in atherosclerosis. These conditions include coronary artery disease, restenosis after bypass surgery, incidence of first mycardial infarction (MI; fatal and non-fatal), peripheral vascular disease, and presenile dementia.

BRIEF DESCRIPTION OF THE DRAWINGS

EXHIBIT 1 is a partial view of a rectangular box holding a one month supply of thirty daily administration packs according to this invention, of which twelve such packs are shown. A conventional cover for such a box is not shown.

EXHIBIT 2 shows a label printed on one side of or affixed to a daily administration pack according to this invention as illustrated in EXHIBIT 1.

DESCRIPTION OF THE PREFERRED EMBODIMENTS

The daily administration pack according to this invention can be a pouch, plastic wrap, envelope, bottle, flask, or transdermal delivery device comprising a reservoir holding a supply of composition according to the invention and skin enhancer, and an adhesive layer to be in contact with a person's skin.

The material of such pack can be any material that protects the contents and is not affected by the contents, such as cellophane, glass, metal, paper, and plastic.

The composition to be contained in the daily administration pack can be presented in the form of powder, liquid, or shaped unit dosage forms such as tablets, capsules, and caplets in suitable packaging within a box or other suitable container.

In a particularly preferred embodiment, the daily administration pack can be a pouch made up of two sheets of aluminum foil or cellophane approximately 3 by 3 inches, heat sealed together after inserting the composition to be administered daily in the form of one or more tablets.

The amount of ASA acetylsalicylic acid can range from 41 mg to 500 mg; 81 mg is particularly preferred. Higher doses prevent flushing in those thereto predisposed.

Vitamin B6 improves abnormal responses to methionine loading, especially in combination with folic acid. The dosage can range from 25 mg to 500 mg.

Folic acid at 650 micrograms per day lowered homocystine levels by about 50% in subjects with initially elevated levels, about as good an effect as seen with higher doses. However, the dosage can range from 300 micrograms/day to 1 milligram/day. At folate intake higher than 1000 micrograms/day, there is concern that the hematologic manifestation of unrecognized vitamin B12 deficiency will be masked. Hence the need to prevent the possibility of masking a B12 deficiency by providing this vitamin in adquate quantities of 100 to 1000 milligram/day.

Niacin and niacinamide from 100 mg to 3000 mg/day are therapeutic in increasing dosages limited by the flushing response seen in higher dosages. Different dosages can be used depending on the tolerance of the patient, whether the niacin is time-release or slow-release and whether the flushing is prevented by the prior use of ASA.

Vitamin E antioxidant can be from 100 to 800 IU with maximal in vitro effect noted at 800 IU. Vitamin E can be as an oil, powder, or in liquid form.

Vitamin C antioxidant can be used if desired. A dosage from 500 mg to 2000 mg is preferable and can be in the form of powder, liquid, or crystal.

It is a feature of this invention that preferred levels of ASA in the daily administration pack include quantities well below the 325 mg of a standard adult ASA tablet while preferred levels of vitamins and antioxidants include quantities well above the nutritionally recommended daily allowances (RDA).

EXAMPLE 1
Preparation of Daily Administration Pack

Tablets were prepared containing, in each tablet, the following amounts of active ingredients according to this invention.
ASA 81 milligrams
B6 50 milligrams
B12 100 milligrams
Vitamin C antioxidant 500 milligrams
Vitamin E antioxidant 400 International Units (IU)
Folic acid 900 micrograms
Niacin 500 milligrams
together with excipient and colorant inert ingredients.

A sealed pack for daily administration contained a single tablet as described.

EXAMPLE 2
Prevention of Coronary Heart Disease

BJR, a 48 year old postmenopausal woman had a family history of acute MI's on her father's and mother's side. She volunteered to take one pack according to Example 1 per day and at age 85 she is expected to have no evidence of coronary heart disease.

EXAMPLE 3
Prevention of Elevated Homocystine Level

AM, a 61 year old man was found to have an elevated homocystine level and volunteered to ingest one pack according to Example 1 per day. His homocystine level was normalized within ten days.

EXAMPLE 4
Prevention of Restenosis

ER, a 74 year old woman had restenosis after bypass surgery for coronary artery disease. After volunteering to take one daily pack according to Example 1 daily after her second angioplasty, there was no restenosis

EXAMPLE 5
Preparation of Daily Administration Pack Containing Multiple Tablets Daily administration packs were prepared containing a separate tablet for each active ingredient according to this invention in the amounts stated below:
ASA 81 milligrams
B6 50 milligrams
B12 100 milligrams
Vitamin C antioxidant 500 milligrams
Vitamin E 800 IU
Folic acid 900 micrograms
Niacin 500 milligrams
together with excipient and colorant inert ingredients.

EXAMPLE 6
Prevention of Flushing

RR, a 71 year old woman had flushing from taking niacin for high density LDL. When taking ASA from a daily administration pack according to Example 5 prior to the niacin, her flushing reaction was minimized.

EXAMPLE 7
Improved Compliance

IT, a 68 year old male diabetic with severe peripheral vascular disease was on twelve medications for his diabetes and could not remember to take in addition one pill from each of six bottles on a daily basis to prevent against progressive atherosclerosis. The daily administration pack according to Example 1 improved compliance 100%.

EXAMPLE 8
Preparation of Daily Administration Pack in Liquid Form

A liquid daily administration pack was prepared containing, in each 2 milliliters the following amounts of active ingredients according to this invention
ASA 81 milligrams
B6 50 milligrams
B12 100 milligrams
Vitamin C antioxidant 500 milligrams
Vitamin E antioxidant 400 IU
Folic acid 900 micrograms
Niacin 500 milligrams
and sufficient water to the indicated volume.

EXAMPLE 9
Prevention of Dementia

A 50 year old woman with a family history of atherosclerotic familial dementia volunteered to take daily a liquid daily administration pack according to Example 8. The onset of dementia is not expected.

EXAMPLE 10
Preparation of Daily Administration Pack For Transdermal Administration A cream was prepared containing in each tablespoonful the following amounts of active ingredients according to this invention.

ASA 81 milligrams
B6 50 milligrams
B12 100 milligrams
Vitamin C antioxidant 500 milligrams
Vitamin E antioxidant 400 IU
Folic acid 900 micrograms
Niacin 500 milligrams
together with water, lecithin, cetylstearyl alcohol and medium chain triglyceride to facilitate passage through the skin.

EXAMPLE 11
Prevention of Hypertension

A 51 year old man with familial systolic hypertension secondary to atheroscerosis volunteered to take daily a transdermal administration pack according to Example 10. His blood pressure is expected to remain normal as long as treatment continues.

EXAMPLE 12
Treatment of Claudication

OK, 67 year old man with claudication for two years secondary to peripheral vascular disease volunteered to take daily a daily administration pack according to Example 1. After on e year of therapy, his claudication symptoms improved 65%.

The foregoing description is intended as illustrative and is not to be taken as limiting. Still other variations within the spirit and scope of this invention as defined by the claims are possible and will readily present themselves to those skilled in the art.

What is claimed is:

1. The method of reducing the severity of atherosclerosis, atherosclerotic central nervous system disease, claudication, coronary artery disease, homocystine related disorders, hypertension, peripheral vascular disease, presenile dementia and/or restenosis in humans by daily administration of an effective amount of a combination consisting essentially of acetylsalicylic acid (ASA), at least one antioxidant, a cyanocobalamin compound (Vitamin B12), a folic acid compound, a pyridoxine compound (Vitamin B6) and a niacin compound.

2. The method of claim 1 in which ASA is any one or more of free acetylsalicylic acid, buffered aspirin, or enteric coated aspirin in a unit dose of 41 milligrams to 500 milligrams expressed as free aspirin.

3. The method of claim 1 in which the antioxidant is at least one Vitamin C compound which is one or more of free ascorbic acid, buffered ascorbic acid, calcium ascorbate, magnesium ascorbate, ascorbyl palmitate, and Vitamin C-associated bioflavanoids in a unit dose of 500 milligrams to 2000 milligrams expressed as free ascorbic acid.

4. The method of claim 1 in which the antioxidant is at least one Vitamin E compound which is one or more of alpha-tocopherol, natural d-alpha-tocopherol with mixed tocopherols including beta-tocopherol, delta-tocopherol, and gamma-tocopherol and Vitamin E dl alpha tocopheryl acetate in a unit dose of 400 International Units to 800 International Units expressed as Vitamin E activity.

5. The method of claim 1 in which the Vitamin B12 compound is in a unit dose of 100 milligrams to 1000 milligrams, the folic acid compound is free folic acid in a unit dose of 300 micrograms to 1 milligram expressed as free folic acid, and the Vitamin B6 compound is pyridoxine hydrochloride in a unit dose of 25 milligrams to 100 milligrams.

6. The method of claim 1 in which the niacin compound is any one or more of nicotinic acid, nicotinamide, slow release niacin, and niacin combined with prostaglandin inhibitor in a unit dose of 100 milligrams to 3000 milligrams expressed as nicotinic acid.

7. The method of claim 1 in which administration of the combination is by mouth.

8. The method of claim 1 in which administration of the combination is transdermal.

9. A daily administration pack for reducing the severity of atherosclerosis, atherosclerotic central nervous system disease, claudication, coronary artery disease, homocystine related disorders, hypertension, peripheral vascular disease, presenile dementia and/or restenosis in humans consisting essentially of a combination of an effective amount of acetylsalicylic acid (ASA), an effective amount of at least one antioxidant, an effective amount of a cyanocobalamin compound (Vitamin B12), an effective amount of a folic acid compound, an effective amount of a pyridoxine compound (Vitamin B6) and an effective amount of a niacin compound.

10. A daily administration pack according to claim 9 in which ASA, antioxidant, Vitamin B6, Vitamin B12, folic acid and niacin are combined in a single unit dosage form.

11. A daily administration pack according to claim 9 in which each of ASA, antioxidant, Vitamin B6, Vitamin B12, folic acid and niacin are present in a separate unit dosage form.

12. A daily administration pack according to claim 9 in which niacin is present in a separate unit dosage form and ASA, antioxidant, Vitamin B6, Vitamin B12 and folic acid are combined in a single unit dosage form.

13. A daily administration pack according to claim 9 in which the amount of ASA is 41 milligrams to 500 milligrams expressed as free aspirin, the amount of antioxidant is 500 milligrams to 2000 milligrams expressed as free ascorbic acid and/or 400 International Units to 800 International Units expressed as Vitamin E activity, the amount of Vitamin B6 is 25 milligrams to 100 milligrams expressed as pyridoxine), the amount of Vitamin B12 is 100 milligrams to 1000 milligrams expressed as cyanocobalamin, the amount of folic acid is 300 micrograms to 1 milligram expressed as free folic acid, and the amount of niacin is 100 milligrams to 3000 milligrams expressed as nicotinic acid.

14. A daily administration pack according to claim 9 formulated for transdermal administration by including at least one skin enhancer.

15. A daily administration pack according to claim 14 in which the skin enhancer is lecithin.

16. A composition for reducing the severity of atherosclerosis, atherosclerotic central nervous system disease, claudication, coronary artery disease, homocystine related disorders, hypertension, peripheral vascular disease, presenile dementia and/or restenosis in humans consisting essentially of ASA 81 milligrams B6 50 milligrams B12 100 milligrams Vitamin C antioxidant 500 milligrams Vitamin E antioxidant 400 International Units Folic acid 900 micrograms Niacin 500 milligrams together with 0 to 1000 milligrams of excipient and 0 to 1000 milligrams of colorant inert ingredients.

17. A daily administration pack according to claim 9 which diminishes the severity of atherosclerosis in at least approximately 80% of the general population.

18. A daily administration pack according to claim 17 that further diminishes the need for blood testing or monitoring.

19. A composition according to claim 16 which diminishes the severity of atherosclerosis in at least approximately 80% of the general population.

20. A composition according to claim 19 that further diminishes the need for blood testing or monitoring.

* * * * *

UNITED STATES PATENT AND TRADEMARK OFFICE
CERTIFICATE OF CORRECTION

| | | |
|---|---|---|
| PATENT NO. | : 6,121,249 | |
| APPLICATION NO. | : 09/108765 | |
| DATED | : September 19, 2000 | |
| INVENTOR(S) | : Weissman et al. | |

It is certified that error appears in the above-identified patent and that said Letters Patent is hereby corrected as shown below:

On the title page, Item [75] Inventors:, the name Donald L. Weissman should be changed to Don Weissman MD.

Signed and Sealed this
Fourth Day of June, 2013

Teresa Stanek Rea
*Acting Director of the United States Patent and Trademark Office*